United States Patent [19]

Thaler

[11] 4,091,817
[45] May 30, 1978

[54] P-WAVE CONTROL, R-WAVE INHIBITED VENTRICULAR STIMULATION DEVICE

[75] Inventor: Sherwood Sheldon Thaler, Calabasas, Calif.

[73] Assignee: American Optical Corporation, Southbridge, Mass.

[21] Appl. No.: 726,887

[22] Filed: Sept. 27, 1976

[51] Int. Cl.² .............................................. A61N 1/36
[52] U.S. Cl. .............................................. 128/419 PG
[58] Field of Search ............ 128/419 PG, 419 R, 421, 128/422, 423

[56] References Cited

U.S. PATENT DOCUMENTS

| 3,253,596 | 5/1966 | Keller, Jr. | 128/419 PG |
| 3,433,228 | 3/1969 | Keller, Jr. | 128/419 PG |
| 3,648,707 | 3/1972 | Greatbatch | 128/419 PG |
| 3,783,878 | 1/1974 | Thaler et al. | 128/419 PG |
| 3,794,045 | 2/1974 | Thaler | 128/419 PG |
| 3,807,410 | 4/1974 | Wall et al. | 128/419 PG |
| 3,903,897 | 9/1975 | Woollons et al. | 128/419 PG |

OTHER PUBLICATIONS

Fischler et al "IEEE Transactions on Biomedical Engineering", v. BMG16 #1, Jan. 1969, pp. 64-68.

*Primary Examiner*—William E. Kamm

[57] ABSTRACT

A heart pacer is presented wherein detection of P-waves from the wave complex is used to control the rate of ventricular stimulation by the pacer, where the control of the rate of the pacer (or the escape interval of the pacer) includes decreasing rates and may also include increasing rates. The pacer of the preferred embodiment is a demand pacer of the R-wave inhibited variety. The circuitry is capable of being implanted within the body of the patient as well as being employed in an external manner.

14 Claims, 6 Drawing Figures

P-WAVE CONTROL, R-WAVE INHIBITED VENTRICULAR STIMULATION DEVICE

BACKGROUND OF THE INVENTION

1. Field of the Invention

The present invention relates generally to heart-stimulation devices, and particularly to R-wave inhibited, P-wave rate controlled devices.

2. Description of the Prior Art

In the field of medical electronics, heart pacers are becoming widely accepted and well known at this juncture. There are several varieties of heart pacer available on the market today. There are pacers which provide stimulation to the ventricle of the heart at a fixed rate, pacers which provide stimulation to the ventricle of the heart on demand, pacers which provide stimulation to the atrium and ventricle of the heart in a predetermined timing sequence and on demand, and pacers which provide stimulation to the ventricle in response to signal inputs received from the patient's body other than from the ventricular chambers of the patient's heart. (By no means is this listing intended to include all types of pacers available today.) It is with this last mentioned type of heart pacer that the present invention is more particularly related.

In some prior art, signal inputs from the thorax, such as an electrical signal analogous to breathing rate, is described to control the stimulation rate of the device. In other prior art even more closely related to the present invention, sensing of the P-wave is used to control the time when ventricle stimulation can occur. For instance a device is known which can detect P-waves and which causes a ventricular pulse generator to supply a stimulation pulse at a fixed interval of time after the P-wave detection occurred. If no P-wave occurs, the pacer provides a stimulation pulse to the ventricle of the heart at the end of a predetermined interval from the previous ventricular heart beat or stimulation. If a P-wave is sensed at or near the time of occurrence of the ventricular stimulation impulse, the ventricular stimulation impulse still occurs at the expected time. There is thus an upper limit on the interval between the ventricular stimulation impulses, or in other words, a lower limit to rate.

But consider the effect of the P-wave occurring early in the escape interval. The ventricular stimulation impulse is thus made to occur at a fixed interval after the detection of the P-wave and is thus earlier than otherwise it would have occurred. Accordingly, such prior art represents only a shortening of the escape interval (or in other words, a speed-up of the stimulation rate), but does not provide a slowing down of the rate when it would be desirable to do so, for example when a patient tries to relax or sleep. If the pacer is provided with a basic rate sufficiently slow to accommodate relaxation or sleep and may "speed-up" therefrom in response to P-wave rate increase, there remains the problem of P-wave generation and/or detection results in reversion to a basic rate which is too slow to be acceptable and may require surgical replacement.

Another pacer which operates in a somewhat similar manner is also known in the prior art. There too, however, the ventricular stimulation pulses occur at a certain basic rate in a "free-running" mode and the atrial pulses and accompanying circuitry operate only to accelerate the ventricular stimulation pulse rate (i.e. decrease the escape interval).

SUMMARY OF THE INVENTION

In accordance with the invention there is provided a heart-stimulating device or pacer having terminal means for connection to a patient's heart, timing circuitry for at least establishing timing intervals which are at least as long as a basic interval, pulse generating circuitry for generating a ventricular stimulation impulse on the terminal means at the end of each of the timing intervals, a P-wave detector for detecting the beating action of the heart's atrium, circuitry responsive to the P-wave detector for generating an atrial-ventricular (A-V) interval pulse, the timing circuitry including control circuitry responsive to the A-V interval pulse for at least lengthening the timing interval beyond the basic interval if the otherwise next generated ventricular stimulation impulse would have occurred during the time of occurrence of the A-V interval pulse and for limiting the lengthened interval to be no longer than the sum of the basic interval and the interval of the A-V interval pulse, an R-wave detector for detecting the beating action of the heart's ventricle, and circuitry responsive to the operation of the R-wave detector for resetting the timing means. The timing circuitry includes a relaxation oscillator in which the basic timing interval is determined by a timing capacitor charging to a basic threshold voltage level. By temporarily adjusting the threshold voltage level the timing interval of the oscillator is extended (and alternatively, contracted) relative to the basic interval, thereby to reduce (and alternatively, increase) the stimulation rate. As used herein, the A-V interval pulse refers to an electrical signal whose duration corresponds with the desired A-V interval.

In an embodiment of the invention the adjustment of the threshold voltage level is accomplished by adding a component voltage thereto for an interval corresponding with that of the A-V interval pulse, and thus, the desired A-V interval. In fact, in a basic embodiment the A-V interval pulse is additively applied to the threshold or reference terminal of the relaxation oscillator. The pulse is of sufficient magnitude to extend the pacer's escape interval to the sum of the basic interval and the A-V interval if a P-wave is detected late in the basic interval. This extended interval corresponds with a reduction in the stimulation rate relative to that afforded at the basic timing interval.

In a further embodiment of the invention, the A-V interval pulse is extended to the threshold voltage terminal of the relaxation oscillator through a coupling capacitor which is sized to cause a predetermined droop in the voltage appearing at the terminal during the A-V interval. When the A-V pulse undergoes a voltage down-step at the end of the A-V interval, the capacitor exhibiting the droop, because only partially charged, acts to temporarily reduce the voltage at the threshold terminal to a value below the basic threshold level. This downwardly adjusted threshold voltage may fire the relaxation oscillator if it occurs within a particular interval immediately preceding expiration of the basic escape interval, thereby increasing the pacer stimulation rate. In a preferred embodiment, the coupling capacitor and included timing circuitry are scaled such that the basic timing or escape interval may be alternatively automatically extended by an interval which may be as great as the A-V interval or contracted by an interval which may be as great or greater than the A-V interval to provide stimulation pulses occurring at the completion of the fixed A-V interval following detection of P-waves occurring over a range.

Both the R-wave and P-wave detectors may be remotely disabled to enable pacer operation in the known continuous mode with stimulation pulses at the basic escape interval.

The pacer of the invention is accordingly responsive to P-wave control for generating a stimulation pulse (unless R-wave inhibited) following a fixed A-V interval, and the pacer is automatically capable of slowing the stimulation rate from a preferred basic rate to which it otherwise reverts in the event P-waves are not effectively detected.

DESCRIPTION OF THE PREFERRED EMBODIMENTS

Figure 1:
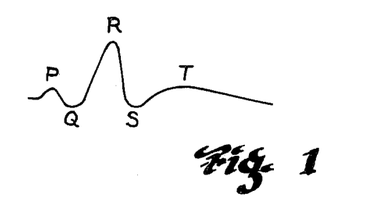
FIG. 1 illustrates the voltage wave produced by the heart during one complete heartbeat.

The human heartbeat is represented electrically as a complex wave consisting of what are designated P,Q,R,S and T waves as shown in FIG. 1. The P-wave represents an atrial beat associated with atrial depolarization, which beat commands the heart rate as a function of signals from the rest of the body. The major and most pronounced electrical pulse in the heart is the R-wave and is normally of a magnitude between 2-20 millivolts in the ventricle. The R-wave, which represents ventricular contraction, typically has an amplitude relation to the P-wave of at least 3:1; although it will be appreciated that the P-wave may be of equal or greater magnitude than the R-wave if both are sensed in the atrium. The R-wave normally represents depolarization of the ventricles, but when not occurring due to some cardiac malfunction, it is a function of the artificial pacer to provide periodic electronic pulses to the heart to stimulate contraction. If both the natural and artificial pacer supply an R-wave, however, competition for control of the heart results and a possibly dangerous situation arises when the pacer electronic pulse occurs in a T-wave region or so called "vulnerable." To avoid this problem, there has been developed a so-called demand pacer as typified in U.S. Pat. No. 3,528,428, the subject matter of which is incorporated herein by reference.

Figure 5:
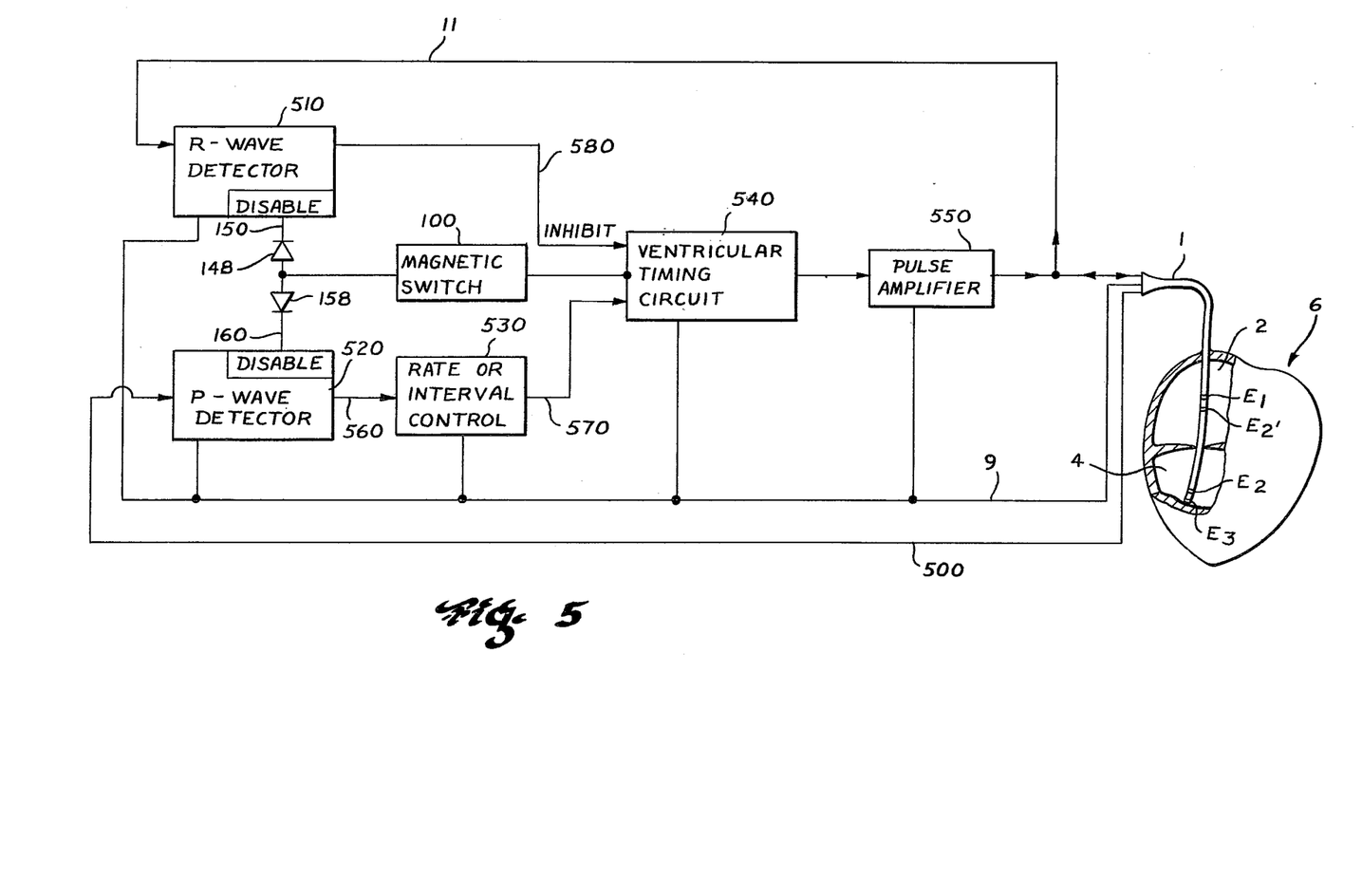
FIG. 5 is a block diagram illustrating a preferred embodiment of the pacer of the invention.

Referring to FIG. 5, there is illustrated in diagrammatic form an artificial pacer constructed in accordance with the invention and having a catheter 1 operatively connected thereto for positioning electrode pole E1 and E2 in the atrium 2 and electrode poles E2 and E3 in the ventricle 4 of heart 6. The catheter 1 is inserted into the heart 6 until its electrode pole tip E3 lodges in the apex of the ventricle. Electrode pole E2 in the ventricle 4 is closely spaced from electrode pole E3, and similarly electrode pole E2' in the atrium 2 is closely spaced from electrode pole E1. The spacing between electrode poles E1 and E3 is preferably about 11 centimeters such that pole E3 contacts the apex of ventricle 4 and electrode E1 is spaced relatively distantly therefrom in the atrium 2. This degree of spacing between electrodes E1 and E3 is preferred in order to maximize the sensing of the P-wave. Myocardial implantation of the electrodes will, of course, provide a suitable alternative, as will the use of separate transvenous electrodes.

Electrode pole E1 is connected through conductor 500 to the input of a P-wave detector 520 for conveying sensed P-waves thereto. Similarly, the ventricular QRS complex sensed by electrode pole E3 is conveyed by conductor 11 to the input of an R-wave detector 510. Conductor 11 additionally extends to the output of pulse amplifier 550 of the pacer from which it receives the ventricular stimulation pulses applied to ventricle 4 by means of electrode pole E3. Electrode poles E2' and E2 in the atrium 2 and the ventricle 4 respectively are connected electrically in common to conductor 9 to provide a common or "ground" electrical reference level connected to the respective portions of the pacer. The R-wave detector 510 and P-wave detector 520 are capable of providing pulses indicative of the detection of a QRS complex and a P-wave respectively. While it may be possible to use the P-wave and R-wave detectors described in either of U.S. Pat. Nos. 3,648,707 or 3,903,897, these detectors in the preferred embodiment are constructed in accordance with the teachings of the aforementioned U.S. Pat. No. 3,528,428. The present R-wave detector 510 is substantially identical to the QRS complex detection circuitry and rate discriminator stage of the aforementioned U.S. Pat. 3,528,428, as will become hereinafter apparent. The P-wave detector 520 is essentially the same as the R-wave detector circuitry 510, each detector including band-pass filters, however the filters associated with the amplifying stages of P-wave detector 520 are scaled to have a somewhat higher pass-band center frequency than the filters of the R-wave detector (e.g. 80Hz vs. 40 Hz). The pass-band center frequencies of detectors 510 and 520 are selected to optimize their sensitivity and response to the QRS complex and the P-wave respectively. It should also be understood that while the aforementioned U.S. Pat. No. 3,528,428 refers to the P-wave as being comprised of frequency components below 20 Hz for the most part, this is true in the ventricle where the electrode senses an integrated form of the P-wave. On the other hand, electrode $E_1$ of the present invention, is positioned in the atrium where the definition of the P-waves is greater, and the P-waves are generally comprised of frequency components of about 80 Hz.

Figure 2:
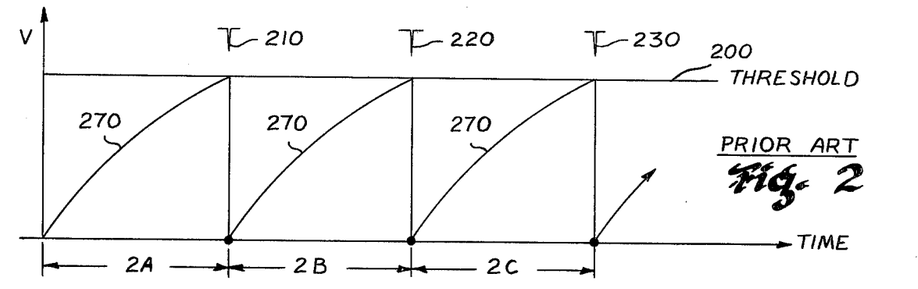
FIG. 2, waveforms 2A-2C comprise a sequential graphical representation of the voltage appearing across the timing capacitor of the pacer's relaxation oscillator relative to the threshold voltage for controlling the generation of stimulation pulses, as known in the prior art.

Ventricular timing circuit 540 is operative in a free running or continuously operating mode, known in the prior art, to provide pulses recurring at a regular or so-called "basic" interval, as illustrated by pulses 210, 220 and 230 waveforms 2A, 2B and 2C respectively of FIG. 2, those pulses being amplified by pulse amplifier 550 and applied to electrode E3 through conductor 11 for stimulation of the ventricle 4. The ventricular timing circuit 540 is essentially comprised of a relaxation oscillator having a basic timing interval in the free running mode and which is inhibited by a reset pulse on conductor 580 from R-wave detector 510 each time an R-wave appears on conductor 11, as required for "demand" operation. The rate or interval controller 530 forms part of the general pacer timing circuitry through conductor 570 and is responsive to pulses appearing on conductor 560 from the output of P-wave detector 520 each time an atrial P-wave is detected for adjusting or controlling the timing of ventricular timing circuit 540.

Through the appropriate selection of components and their values in interval control circuit 530 and in conjunction with the circuitry of ventricular timing circuit 540, the pacer of the invention is capable of adjusting the timing of circuit 540 such that the ventricular stimulation impulses normally occur following a predetermined fixed delay or interval (termed the A-V interval) after the occurrence of a detected atrial P-wave such that the interval between successive ventricular stimulation pulses may at least be increased relative to the regular or basic interval in accordance with a decreased atrial P-wave rate. Additionally, the interval control 530 may also be capable of decreasing the interval between successive ventricular stimulation pulses relative to the basic interval for an increase in the rate of said atrial P-wave.

Accordingly, the basic timing interval of ventricular timing circuit 540 may be established as that providing a stimulation pulse rate of about 75 beats per minute, and the P-wave rate may then act to slow this rate as for relaxation or sleeping and additionally may act to accelerate the rate as during exercise. Thus it is evident that even if the P-wave detection and interval controlling circuitry added by the invention is ineffective, as due to the absence of atrial P-waves or a failure in that processing circuitry, the pacer will continue to operate as a conventional demand pacer at a stimulation rate (75 beats per minute) which is clearly adequate for life support and well within the upper and lower limits.

A selectively actuable switch 100 is operatively connected with the ventricular timing circuit 540 and its associated power source, and also with respective DISABLE inputs on R-wave detector 510 and P-wave detector 520 in order to selectively reduce output pulse amplitude, increase the rate of stimulation pulses, and stimulate the pacer continuously in the manner heretofore known and described in U.S. Pat. No. 3,774,619. The pacer of the illustrated embodiment is preferably an implantable pacer and switch 100 is a magnetically actuated reed switch.

Figure 6:
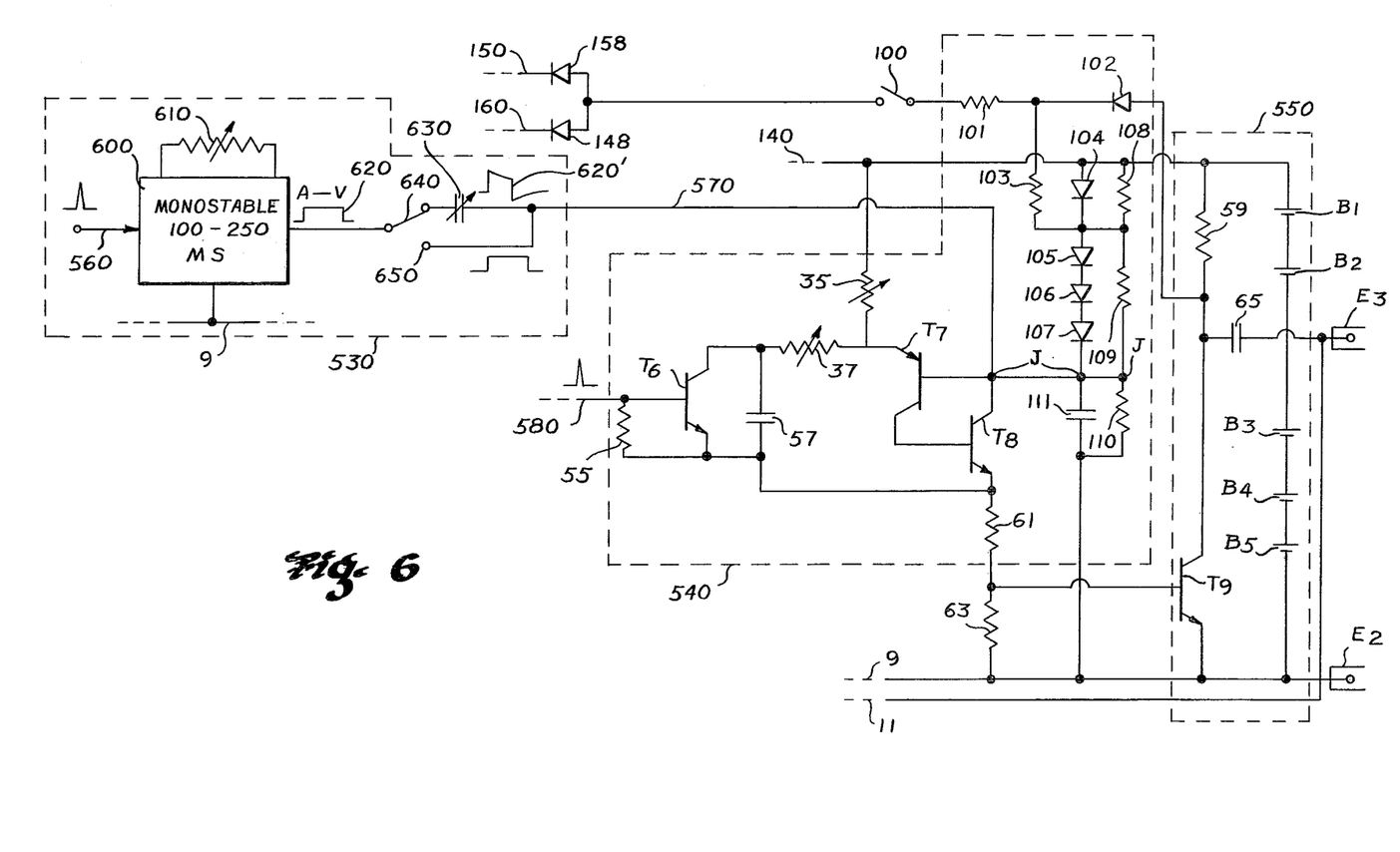
FIG. 6 is a more detailed circuit diagram of portions of the pacer illustrated in FIG. 5.

Reference is now made to FIG. 6 which is a schematic of the illustrative embodiment of the present invention. The schematic of FIG. 6 is to be viewed in conjunction with FIG. 1 of the aforementioned U.S. Pat. 3,528,428, the exact combination of which provides an operative embodiment except for the inclusion of P-wave detector 520. Accordingly, to the extend that the U.S. Pat. No. 3,528,428 is incorporated for its disclosure of R-wave detector 510, it is similarly incorporated for the teaching of a detector such as P-wave detector 520 which differs from the R-wave detector 510 in only the relatively few ways mentioned. The following components of FIG. 6 of the instant application are identical to components of FIG. 1 of this patent: the transistors T6, T7, T8, and T9; resistors 35, 37, 55, 61, 63 and 59; capacitors 57 and 65; electrodes E1 and E2; and conductors 9 and 11. Interconnection of these components is described in this patent. Other components in FIG. 6 of the instant application may be equivalent to components in FIG. 1 of this patent, but are given different reference numerals.

In addition to that material disclosed in U.S. Pat. No. 3,528,428 which is incorporated herein by reference, certain other portions of the pacer as illustrated in FIG. 6 are described in U.S. Pat. No. 3,774,619 to which reference may be made for additional information. The following components of FIG. 6 of the instant application are substantially identical to the components of FIG. 2 of U.S. Pat. No. 3,774,619: the transistors T7, T8 and T9; resistors 59, 61, 63, 101, 103, 108, 109 and 110; diodes 102, 104, 105, 106 and 107; switch 100; capacitors 65 and 111; and batteries B1-B5.

With references to FIG. 6, showing component interconnection, the anode of diode 102 is connected to the junction of resistor 59, and capacitor 65. The cathode of diode 102 is connected to the junction of resistors 101 and 103. The other end of resistor 101 is connected to one end of an externally operated implantable magnetic reed switch 100. The other end of reed switch 100, the fixed end, goes to the anodes of diodes 148 and 158 in turn having respective conductors 150 and 160 extending from the cathodes thereof to the DISABLE inputs of R-wave detector 510 and P-wave detector 520 respectively.

The other end of resistor 103 is connected to a junction comprised of a cathode of diode 104, the anode of diode 105, and resistors 108 and 109. Diodes 104 and resistor 108 are in parallel connection. Diodes 105, 106 and 107 are in a series string and are in a parallel connection with resistor 109. The junction of resistor 109 and the cathode of diode 107 are connected to one end of the parallel combination of capacitor 11 and resistor 110, the other end of which parallel combination is connected to conductor 9. The junction of resistors 109 and 110 (junction J) is connected to the base of transistor T7. The potential of this junction is the threshold level of the timing circuitry and will be discussed below in detail.

In accordance with the invention, the P-wave detector 520 and a rate or interval control 530 are operatively connected to junction J of the pacer timing circuitry to adjust the threshold potential level threat in response to the detection of atrial P-waves in heart 6. The interval control 530 as illustrated in FIG. 6 includes a monostable multivibrator or one-shot 600 for generating an A-V interval pulse in response to a trigger pulse received from the output of P-wave detector 520. The variable resistor 610 enables the monostable 600 to be controlled to provide an A-V delay pulse having an interval within the range of 100-250 milliseconds.

The A-V interval pulse 620 at the output of monostable 600 is of conventional, rectangular waveform and, in one embodiment of the invention, is connected substantially directly to junction J. In another embodiment of the invention A-V interval pulse 620 is extended to junction J through a capacitor 630 to obtain a preselected "droop" in the pulse waveform voltage applied to junction J. While these two embodiments might normally appear in separate pacers, in the interest of brevity they have been combined in FIG. 6 and illustrated as being available in a single pacer through use of a presettable single pole, double throw switch 640.

One pole of switch 640 is connected to the output of monostable 600 and the other pole is selectively connectable either to one end of capacitor 630 (as shown) or to terminal 650 of a bypass conductor connected to the conductor 570 and the other end of capacitor 630.

Also for the purpose of illustrating the invention, the capacitor 630 is shown as being variable to illustrate that the extent of droop introduced to A-V delay pulse 620 may vary, as will be described.

Interrelating the circuitry of the instant application with U.S. Pat. No. 3,528,428, conductor 150 is connected to the emitter of transistor T1 in FIG. 1 of that patent. Conductor 140 is connected to the junction of resistors 29, 31 and 33 in that patent. Conductor 580 is connected to the side of capacitor 53 remote from the side which is connected to the junction of capacitor 49 and resistors 47 and 45 in that patent. In this illustrative embodiment of the present invention, switch S of FIG. 1 of that patent is omitted (i.e. consider switch S to be held open at all times). In addition to the above interrelations of the circuitry of FIG. 6 of the instant application with that patent, conductor 160 from diode 168 is connected to the emitter of a transistor in the P-wave detector 520 which is comparable to transistor T1 in FIG. 1 of this patent.

Briefly considering the operation of components 100–111 in the illustrated pacer with switch 100 open as shown, current from the series string of batteries flows through resistor 59 and charges up capacitor 65 which holds the voltage as long as transistor T9 is not turned on. Current from the series string of batteries also flows through the parallel combination of diode 104 and resistor 108; the individual currents of that parallel branch combine to flow almost exclusively through resistor 109. Resistor values of resistors 108, 109 and 110, which form a voltage divider, are chosen to keep voltage across diodes 105, 106 and 107 below their combined forward voltage drop. Diodes 105, 106 and 107 are used only to counteract adverse transients during turn on and can be ignored without sacrificing any understanding of the operation of the instant invention.

With switch 100 open as shown, the demand mode of operation is permitted. If the heart demands a stimulating impulse, transistors T7 and T8 cause transistor T9 to conduct, causing capacitors 65 to discharge through ventricular electrodes E2, E3, and the heart 6. The transistors T7 and T8 comprise a relaxation oscillator which is timed by the rate at which capacitor 57 charges to the threshold voltage level appearing at the base of transistor T7 (junction J). When the voltage on capacitor 57 is such that the timing voltage 270 on the emitter of transistor T7 is equal to that on its base (junction J), the relaxation oscillator is triggered, causing transistor T9 to conduct. Transistor T6 is connected across timing capacitor 57 and is responsive to a pulse on conductor 580 from capacitor 53 each time an R-wave is detected for conducting and thereby discharging and resetting capacitor 57. In this manner, detected R-waves act to reset the relaxation oscillator before completion of a basic interval or cycle in order to prevent a ventricular stimulation impulse from being generated during the vulnerable period following a ventricular contraction.

When T8 conducts, some of the current for the collector of T8 comes from the charged capacitor 111. After T8 stops conducting capacitor 111 recharges to its former state through resistors 108 and 109. Capacitor 111 is chosen so that it does not recharge to its previous static voltage value in a time equal to or less than the time between pulses in the ordinary heart rate to provide what is known in the prior art as rate hysteresis.

Diode 104 is a compensating diode which compensates for non-linear base emitter voltage drop of transistor T7 when the batteries start to diminish in voltage, as known in the prior art, and is presented herein only for the purpose of completeness.

Reference is now made to those portions of the pacer of the invention which are responsive to atrial P-waves for controlling the ventricular stimulation pulse rate in the novel manner of the invention. The P-wave detector 520 responds to each P-wave by generating a trigger pulse which is applied to the triggering input of monostable 600 via conductor 560. The input to monostable 600 is connected to one side of a capacitor (not shown) which is analogous to capacitor 53 in the R-wave detection circuitry of U.S. Pat. No. 3,528,428. While the trigger pulse applied to monostable 600 is herein illustrated as being positive, it will be appreciated that a pulse of opposite polarity might be provided if required by monostable 600.

In the illustrated embodiment, the A-V pulse 620 provided by monostable 600 is of a duration or interval determined by the setting of variable resistor 610. An atrialventricular delay or escape interval of about 200 milliseconds is considered suitable in the present embodiment and accordingly, is adopted for purposes of further discussion.

Figure 3:
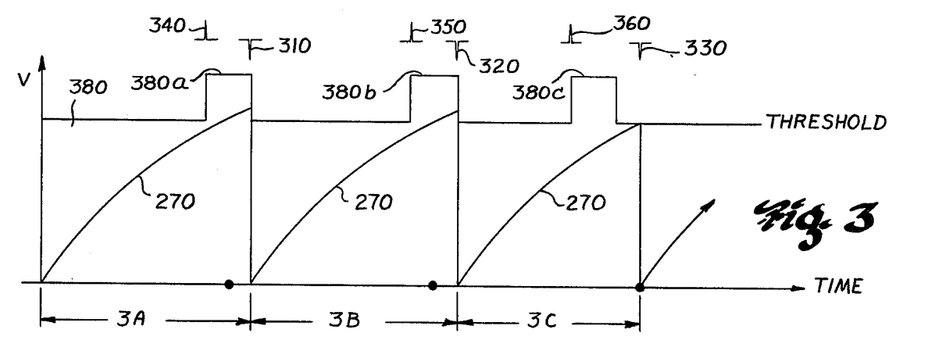
FIG. 3 waveforms 3A-3C comprise sequential graphical representations similar to FIG. 2 and showing the threshold voltage modified in accordance with one aspect of the invention.

Assuming initially a connection of switch 640 to terminal 650, the A-V pulse 620 is connected directly to junction J at the base of transistor T7 while bypassing capacitor 630. Accordingly, the increased voltage of a pulse 620 is added to the normal threshold voltage 380 appearing at junction J such that the threshold voltage illustrated in waveforms 3A 3B and 3C respectively of FIG. 3 is elevated during the A-V pulse interval as indicated by portions 380a, 380b and 380c respectively of the threshold voltage.

For instance in waveform 3A, a P-wave represented by pulse 340 occurs about 700 milliseconds after the last resetting of the relaxation oscillator to provide A-V interval pulse 620 which elevates the threshold voltage at 380a for 200 milliseconds such that the timing voltage 270 on the emitter of transistor T7 does not meet the threshold voltage at 800 milliseconds as had been the case in the free running mode of operation illustrated in waveforms 2A–2C. Instead, the threshold voltage is temporarily adjusted upwardly and the timing capacitor 57 continues to charge until, at the completion of A-V pulse 620, the threshold voltage returns to its normal steady state level. During the negative transition to its steady state level, the threshold voltage 380 meets the timing voltage 270 whereupon the ventricular stimulation pulse 310 is generated in the manner previously described. The amplitude of A-V pulse 620 is such that the increased threshold voltage 380a is greater than the normal threshold voltage 380 by an amount greater than the attendant rise in timing voltage 270 during the interval of pulse 620 at that time in the escape intervals to assure the preset A-V interval.

Figure 4:
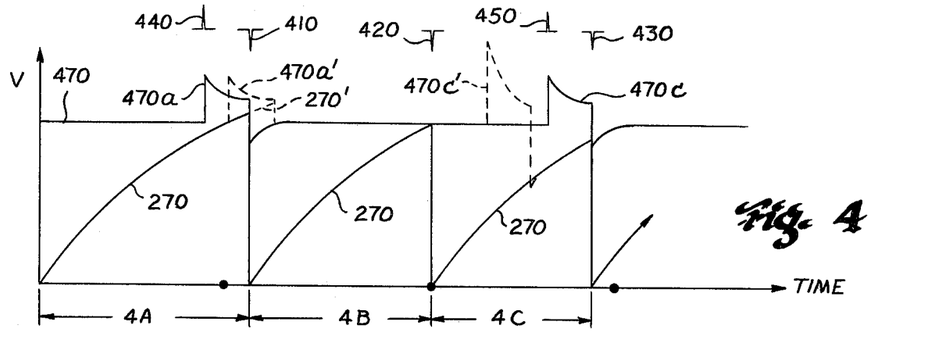
FIG. 4 waveforms 4A-4C comprise sequential graphical representations similar to FIG. 2 showing the threshold voltage modified in accordance with another aspect of the invention.

Thus, the condition represented by waveform 3A is one in which the stimulation impulse escape interval has been extended from the basic 800 milliseconds to 900 milliseconds. This increase in interval is similarly representative of a decrease in stimulation pulse rate as might be required for a period of sleep. Though not shown, it will be appreciated that the ventricular stimulation impulse 310 might have occurred as late as about 3A–1 4A–following the prior resetting of the relaxation oscillator if P-wave 340 had occured as late as 780–795 milliseconds in the escape interval. This would represent the maximum delay in the stimulation pulse escape interval and would be representative of a heart rate of about 60 beats per minutes. Waveform 3B and its P-wave pulse 350 and stimulation pulse 320 are essentially a repetition of waveform 3A for the purpose of illustrating continuance of the adjusted timing interval at the reduced rate. The dots on the time baselines of waveforms 2A-2C, 3A-3C, and 4A-4C represent the expiration of the basic or natural timing interval relative to the time of reset.

Waveform illustrates the situation in which P-wave pulse 360 occurs so soon after the resetting of timing capacitor 57 that the elevated threshold voltage 380c has returned to the normal threshold level 380 before timing voltage 270 has reached that level. This will occur anytime the P-wave occurs earlier than 600 milliseconds into the escape interval, assuming the potential at junction J follows the waveform of waveform, and results in ventricular stimulation pulse 330 being generated at about the end of the basic interval of 800 milliseconds.

While the foregoing arrangement provides improved P-wave control of an R-wave inhibited ventricular stimulation pacer by providing for rate "slowdown" from the natural or basic rate of the pacer, it is possible through the introduction of so-called "droop" in the adjusted threshold voltage level to provide rate "speedup" as well in the same pacer. This operation exists when the A-V interval pulse 620 is connected with junction J through a capacitor having a value selected to provide a requisite degree of "droop".

Referring to waveforms 4A-4C and FIG. 6, when switch 640 is connected with the terminal of capacitor 630 (as shown), the adjustment to the normal threshold voltage 470 at junction J occasioned by A-V interval pulse 620 will initially experience a rise commensurate with the positive step in the pulse 620, followed by a decline or "droop" determined by the value of capacitor 630 in the RC circuit which also includes resistors 108, 109 and 110 and capacitor 111. The resulting modification to the waveform shape of A-V pulse 620, as seen by junction J, is illustrated by the waveform 620' in FIG. 6.

The threshold voltage at junction J remains at the normally constant level 470 throughout the early portion of the escape interval until the occurrence of P-wave pulse 440, at which time the output of monostable 600 provides the positive voltage step A-V pulse 620 which is seen at junction J as a commensurate step increase in the voltage, as indicated by 470a. The capacitor 630 immediately begins to charge at a rate determined by the time constant of the circuit through capacitor 630 and thence through the several parallel paths comprised of serial resistors 108 and 109, resistor 110, and capacitor 111. As capacitor 630 charges, the voltage across it increases bringing about an attendant decrease in the voltage at junction J. The circuitry is scaled such that this decrease or "droop", in voltage by the end of the 200 milliseconds comprising the A-V interval will be something less than 100% of the voltage rise at junction J occasioned by the positive step in A-V pulse 620.

For instance, the greater the capacitance of capacitor 630 in the RC circuit of which it is a part, the slower the charging rate will be, resulting in a lesser degree of droop; whereas a relatively smaller size capacitor 630 will result in a higher degree of droop. In fact, if the capacitance of capacitor 630 is sufficiently large, the droop during the 200 millisecond A-V interval may be so slight as to afford performance substantially as obtained with the earlier described DC connection through terminal 650. The capacitive value of capacitor 111 is small compared to that of capacitor 630 and has very little effect on the latter's charging rate.

At the end of the 200 millisecond A-V interval, the downward voltage step in pulse 620 appears at junction J as a downward voltage step of commensurate magnitude. Because the adjusted threshold 470a has undergone some degree of droop, this downward transition in the threshold voltage carries it below the normal steady state threshold 470 by a voltage corresponding with the voltage droop occurring during "droop". The capacitor 630 then charges in the opposite direction at the rate determined by the time constant of the RC circuit as earlier discussed. This charging continues until capacitor 630 is fully charged and the steady state voltage threshold 470 at junction J is reattained.

So long as the droop is not so great as to cause the declining voltage of the adjusted threshold 470a to equal the increasing timing voltage 270 prior to completion of the 200 millisecond A-V interval, the adjusted threshold voltage 470a possessing droop is capable of extending the basic 800 millisecond escape interval to 900 milliseconds as illustrated in solid waveform and by stimulating pulse 410 or, in fact, to a full 1 second as illustrated by the dotted waveforms 470a' and 270'.

Waveform 4B is included to illustrate the situation in which no P-wave is detected and accordingly, the ventricular stimulation pulse 420 is generated at the completion of the basic escape interval of 800 milliseconds.

The waveform 4C illustrates a further effect of the droop in the adjusted threshold voltage 470c wherein the threshold voltage on its downstep may intersect or equal the increasing timing voltage 270 prior to the timing voltage attaining the normal threshold level 470 at 800 milliseconds into the escape interval. When such equality of the two voltages occurs, the ventricular stimulation pulse 430 is generated, in this instance at about 700 milliseconds into the escape interval for a P-wave pulse 450 occurring at 500 milliseconds. Thus by introducing droop to the adjusted threshold voltage, it is possible not only to extend the escape interval and thereby reduce the heartrate, but also to contract the escape interval to accelerate the stimulation rate, in each instance retaining the preset 200 millisecond A-V interval.

Certain constraints should be considered in the design of the circuitry. For instance, the RC time-constant of the circuit through which capacitor 630 charges should be less than the RC time-constant of the circuit through which the timing capacitor 57 charges in order to avoid the situation in which the P-wave occurs particularly early in the escape interval and the adjusted threshold voltage does not intersect the timing voltage on its downstep at the completion of the 200 millisecond A-V interval but sometime thereafter when the relatively "slower" recovering threshold voltage is met by the more rapidly rising timing voltage 270. In such instance, the A-V interval will be longer than desired and in fact, will vary with the actual timing of the P-wave in the escape interval.

A further consideration is, that for an adjusted threshold voltage of particular magnitude the percentage of droop in that adjusted threshold voltage not be so great that a P-wave occurring shortly before the expiration of the normal 800 millisecond interval results in an adjusted threshold voltage which droops so rapidly that the increasing timing voltage is met before the expiration of the desired 200 millisecond A-V interval.

Further, each beat or stimulation of the ventricle may be sensed by the P-wave detector 520, and thereby result in an A-V pulse (not shown in FIGS. 3 or 4) from monostable 600. However, the A-V pulse would be initiated at the start of the timing cycle and can be made, by design, ineffectual. If desired, blanking logic could be incorporated to prevent activation of monostable 600 for these events.

In an embodiment scaled to provide the voltage-time waveforms of waveforms 4A-4C except for 470c', the timing voltage 270 is seen to have a voltage-vs.-time slope of about 45° near the end of the normal 800 millisecond timing interval and the magnitude of the upward voltage adjustment to the threshold voltage 470 is such that a 50% droop in the adjusted magnitude provides operation in which the basic escape interval may be increased by as much as the interval of A-V pulse 620 and further, may be decreased by that same A-V interval of pulse 620. This results in the basic stimulation rate of 75 pulses per minute being adjustable within the range from 60 pulses per minute to 100 pulses per minute. In each instance, it is the occurrence and detection of the atrial P-wave which determines the rate at which the pacer generates stimulation pulses.

Although the increase in the basic escape interval is limited to the interval of the A-V interval, the reverse need not be true and the illustration in the immediately preceding paragraph is exemplary and not limiting. In fact, a stimulation pulse can be provided at the end of the A-V interval following a detected P-wave occurring at any time prior to the expiration of the basic escape interval simply by increasing the absolute magnitude of the voltage droop such that the downstep of the threshold voltage is great enough to intersect the rising timing voltage 270. This may be accomplished by increasing the voltage amplitude of the A-V interval pulse 620 and/or by increasing the percentage of droop relative to the embodiment previously described, as illustrated by the dotted line waveform of adusted threshold voltage 470c' having increased magnitude. In this way the stimulation rate may be increased to a theoretical limit determined only by the length of the A-V interval; however as a matter of practicality and safety, the adjustment to the threshold voltage will be preselected to limit the maximum rate to something less, possibly in the area of 110-140 pulses per minute. Similarly, by further decreasing the droop, a high rate limit of 85-90 pulses per minute may be obtained. Thus, where the A-V interval pulse is about 200 milliseconds length, a ventricular stimulation pulse occurring at the end of the A-V interval pulse will be provided if the circuit would otherwise have provided a stimulating pulse during an interval which is about twice (i.e. 1.5-2.5 times) the length of the A-V interval and which begins with the beginning of the A-V interval.

Although not specifically illustrated in FIGS. 2-4, it will be appreciated that the occurrence of an R-wave is overriding and will inhibit the generation of a stimulation pulse by resetting the relaxation oscillator and thereby begin anew the basic timing interval.

In addition to the standard mode of operation of the pacer when magnetic switch 100 is open as previously described, there is also possible a so-called magnet mode of operation, explained in U.S. Pat. No. 3,774,619, in which switch 100 is closed by application of a normally continuous magnetic field from a source externally of the patient's body to disable the R-wave and P-wave detects 510 and 520 respectively such that the pacer is forced to operate in a continuous stimulation mode at a rate somewhat greater than determined by the basic escape interval and which increases with diminishing battery voltage.

If the applied magnetic field is caused to pulse at a rate between about two and five pulses per second, the reed switch 100 "makes" and "breaks" at this rate such that it provides a "virtual heartbeat" at this rate to the pacer circuitry, which results in transistor T6 conducting and thereby discharging capacitor 57 long before it could achieve sufficient potential to cause the stimulation pulse to be generated. Thus, a non-stimulated mode during which the physician may conduct a medical examination of the heart unfettered by continuous or sporadic pacer stimulation.

While preferred embodiments of the invention have been shown and described, various modifications and substitutions may be made thereto without departing from the spirit and scope of the present invention. Accordingly, it is to be understood that the present invention has been described by way of illustration and not limitation.

I claim:

1. A heart stimulating device for stimulating the heart of a patient, said device comprising terminal means for connection to said patient's heart, timing means for at least establishing timing intervals at least as long as a basic interval, pulse generator means for generating a ventricular stimulation impulse on said terminal means at end of each of said timing intervals, first means for detecting the beating action of the atrium of said heart, means responsive to the operation of said first detecting means for generating an A-V interval pulse, said timing means including control means responsive to said A-V interval pulse for at least lengthening said timing interval beyond said basic interval if the otherwise next generated one of said ventricular stimulation impulses would have occurred during the time of occurrence of said A-V interval pulse and for limiting said lengthened interval to be no longer than the sum of said basic interval and the interval of said A-V interval pulse, second means for detecting the beating action of the ventricle of said heart, and means responsive to the operation of said second detecting means for resetting said timing means.

2. The heart stimulating device of claim 1 wherein said A-V interval pulse is of predetermined length and the end of each said lengthened timing interval is substantially concurrent with the end of a respective said A-V interval pulse.

3. The heart stimulating device of claim 2 wherein said timing means additionally selectively establishes said timing intervals as shorter than said basic interval, said control means being operative for alternatively shortening said timing interval to less than said basic interval if said detected beating action of the atrium occurs within a predetermined interval ending prior to the end of said basic interval by said length of said A-V interval pulse.

4. The heart stimulating device of claim 3 wherein the end of each said shortened timing interval is substantially concurrent with the end of a respective said A-V interval pulse.

5. The heart stimulating device of claim 4 wherein said predetermined interval is at least as long as said length of said A-V interval pulse whereby said shortened timing interval may be at least as short as the difference between said basic interval and the interval of said A-V interval pulse.

6. The heart stimulating device of claim 5 wherein said predetermined interval is longer than said length of said A-V interval pulse whereby said shortened timing interval may be shorter than the difference between said basic interval and the interval of said A-V interval pulse.

7. The heart stimulating device of claim 2 wherein said timing means includes means for establishing a threshold voltage, means responsive to said A-V interval pulse for adjusting said threshold voltage, capacitive means, means for charging said capacitive means and means for detecting when voltage on said capacitive means is substantially equal to said threshold voltage, said pulse generator means being repetitively responsive to said detection of equal voltages for generating respective said ventricular stimulation impulses and discharging said capacitive means with each generation, and said timing means resetting means also being operative to discharge said capacitive means responsive to the operation of said second detection means.

8. The heart stimulating device of claim 7 wherein the increase in said adjusted threshold voltage is substantially constant for the duration of said A-V interval pulse.

9. The heart stimulating device of claim 7 wherein said A-V interval pulse is a voltage waveform and said means for adjusting said threshold voltage comprises means for extending the voltage of said A-V interval pulse to said threshold voltage establishing means in at least temporarily additive relationship therewith, thereby temporarily increasing said threshold voltage against which said capacitive means voltage is compared.

10. The heart stimulating device of claim 9 wherein said A-V interval pulse voltage extending means comprises an other capacitive means.

11. The heart stimulating device of claim 10 wherein the time-constant of said other capacitive means in combination with said threshold voltage establishing means in such that said adjusted threshold voltage declines from a first increased value to a second value intermediate said first value and the normal said threshold voltage by the end of a respective said A-V interval pulse, said adjusted threshold voltage temporarily assuming a third value immediately after the end of a respective said A-V interval pulse, said third value being less than the normal said threshold voltage by the amount of said decline in said adjusted threshold voltage during said A-V interval pulse, said third value of adjusted threshold voltage temporarily decreasing the voltage of said capacitive means at which said ventricular impulses are generated for additionally alternatively enabling said timing interval to be shortened from said basic timing interval.

12. The heart stimulating device of claim 11 wherein the end of each said shortened timing interval is substantially concurrent with the end of a respective said A-V interval pulse, and said time-constant and accordingly, said second value of adjusted threshold voltage are selected such that said timing intervals may be alternatively shortened or lengthened from said basic interval by as much as the interval of said A-V interval pulse.

13. The heart stimulated device of claim 12 further including selectively operative means for disabling both said atrium beating detection means and said ventricular beating detection means whereby said ventricular stimulation impulses are repetitively generated by said timing means and pulse generator at a single timing interval corresponding with said basic interval.

14. A heart stimulating device for stimulating the heart of a patient, said device comprising terminal means for connection to said patient's heart, means for establishing a threshold voltage, capacitive means, means for charging said capacitive means, means for detecting when voltage on said capacitive means is substantially equal to said threshold voltage, pulse generator means responsive to the operations of said detecting means for repetitively generating ventricular stimulation impulses at varying intervals on said terminal means and discharging said capacitive means with each generation, atrial means for sensing atrial beating of said patient's heart, means responsive to operation of said atrial sensing means for adusting said threshold voltage during a first predetermined time interval substantially smaller than the smallest of said varying intervals, means responsive to said adjusted threshold for controlling said pulse generator means to provide said impulse at the end of said first predetermined time interval if said pulse generator means would otherwise have provided said impulse during a second predetermined interval, said second predetermined interval being about twice the length of said first predetermined interval and beginning with the beginning of said first predetermined interval, ventricular means for sensing ventricular beating action of said patient's heart, and means responsive to the operation of said second sensing means for discharging said capacitive means.

* * * * *